US011793687B1

(12) United States Patent
Alnajjar

(10) Patent No.: US 11,793,687 B1
(45) Date of Patent: Oct. 24, 2023

(54) REMOVABLE RUBBER BRACELET FOR CAST CUTTING

(71) Applicant: GIFTEDNESS AND CREATIVITY COMPANY, Safat (KW)

(72) Inventor: Kholoud H. A. Alnajjar, Safat (KW)

(73) Assignee: GIFTEDNESS AND CREATIVITY COMPANY, Safat (KW)

( * ) Notice: Subject to any disclaimer, the term of this patent is extended or adjusted under 35 U.S.C. 154(b) by 0 days.

(21) Appl. No.: 18/196,867

(22) Filed: May 12, 2023

(51) Int. Cl.
*A61F 15/02* (2006.01)
(52) U.S. Cl.
CPC .................... *A61F 15/02* (2013.01)
(58) Field of Classification Search
CPC ....................................................... A61F 15/02
See application file for complete search history.

(56) References Cited

U.S. PATENT DOCUMENTS 6,363,617 B1 * 4/2002 Frost ..................... A61F 15/02
30/390

* cited by examiner

*Primary Examiner* — Andrew Yang
(74) *Attorney, Agent, or Firm* — Nath, Goldberg & Meyer; Richard C. Litman

(57) ABSTRACT

The removable rubber bracelet for cast cutting is an attachment for a cast cutting saw that greatly reduces the occurrence of both abrasive and thermal injuries to patients during the cast removable process. The rubber bracelet has two parallel, arcuate, generally semicircular bands or arms extending from opposite ends of a crossbar. The bracelet has an inner core of a flexible, malleable, and at least semi-resilient material, such as copper or spring steel, for maintaining the shape of the bracelet, coated by a layer of rubber for protecting the patient's skin. The bracelet has a smaller, saw attachment band adapted for gripping a barrel of the cutting saw, and a larger guard band or arm adapted for being spaced apart from the rear edge of the saw's cutting blade in cantilever fashion to protect the patient from accidental cuts opposite the portion of the blade edge cutting the cast.

9 Claims, 3 Drawing Sheets

REMOVABLE RUBBER BRACELET FOR CAST CUTTING

BACKGROUND

1. Field

This disclosure is directed towards safety guards for cutting tools and instruments, and particularly to a removable rubber bracelet for cast cutting that is removably attachable to the saw used for cutting casts during the cast removal process.

2. Description of the Related Art

As casts are regularly used in orthopedics, cast saws are frequently used to remove those casts. Advancements in cast cutting technology have been made over the years based on economics, efficiency, and medical practitioner experience. Despite the evolution of this technology, patient experience and comfort has come to represent an oversight in its innovation. Hospitals and clinic centers should not ignore the fear of children and the discomfort of adults during the cast removal process. However, while the use of cast cutting saws is deemed a safe cast removal option, there are often complications that arise with the use of cast cutting saws.

Due to many unfortunate injuries while removing the cast, such as skin cuts and burns, that cause many scars and traumas, it has become evident that a need exists for patients' protection that minimizes the fear and discomfort that they go through during the process of cast removal.

Cast saw injuries are thermal or abrasive (or both) in nature. Thermal risk factors in cast injuries include cast saw specifications (including the lack of a vacuum attachment), dull blade usage, cutting in a concavity, thin padding, and overly bulky cast materials. With abrasive injuries, the risk factors are sharp blades, thin padding, and overly boney prominences. Since nearly all clinicians make contact with the skin during cast removal, an appropriate "in-out technique" is critical. Such techniques prevent a hot blade from remaining in contact with the skin for any significant time, greatly reducing the risk of burns. Similarly, using such a technique prevents "dragging the blade" that may pull the skin taut, cutting it.

Cast saws cut material by exerting a sheer force at the corners of their teeth, causing failure of the material being cut. Cast saws use high frequency, small amplitude blade oscillations to cut materials. The small motion arc with which the blade oscillates allows soft tissues to move back and forth with the blade, dissipating the shear forces, and thus preventing injury. However, once the blade encounters a stationary material that is unable to move with the blade's oscillation, shear forces are generated and the fixed material is cut. In theory, this establishes that these devices are capable of preferentially removing the fixed casting material without injuring the skin underneath. Despite their design, iatrogenic cast saw injuries occur within a range of incidence of 0.1% to 0.72%. In addition to direct patient harm, these injuries can have considerable medical-legal costs for the particular incident.

Thus, a removable rubber bracelet for cast cutting solving the aforementioned problems is desired.

SUMMARY

The removable rubber bracelet for cast cutting is an attachment for a cast cutting saw that greatly reduces the occurrence of both abrasive and thermal injuries to patients during the cast removable process. The rubber bracelet has two parallel, arcuate, generally semicircular bands or arms extending from opposite ends of a crossbar. The bracelet has an inner core of a flexible, malleable, and at least semi-resilient material, such as copper or spring steel, for maintaining the shape of the bracelet, coated by a layer of rubber for protecting the patient's skin. The bracelet has a smaller, saw attachment band adapted for gripping a barrel of the cutting saw, and a larger guard band or arm adapted for being spaced apart from the rear edge of the saw's cutting blade in cantilever fashion to protect the patient from accidental cuts opposite the portion of the blade edge cutting the cast.

The removable rubber bracelet can be easily snapped onto the cast cutting saw when cutting the cast and snapped off once the cast is removed. These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The removable rubber bracelet (RRB) is a removable hard rubber piece that can be easily be removed and attached to the cast cutting saw. The purpose of the RRB is to protect the skin from being injured and/or burned by the blade, thus preventing respective abrasive and thermal injuries. The RRB is practical and is reasonably dimensioned and configured to provide skin protection from all angles and shapes of casts.

Figure 1:
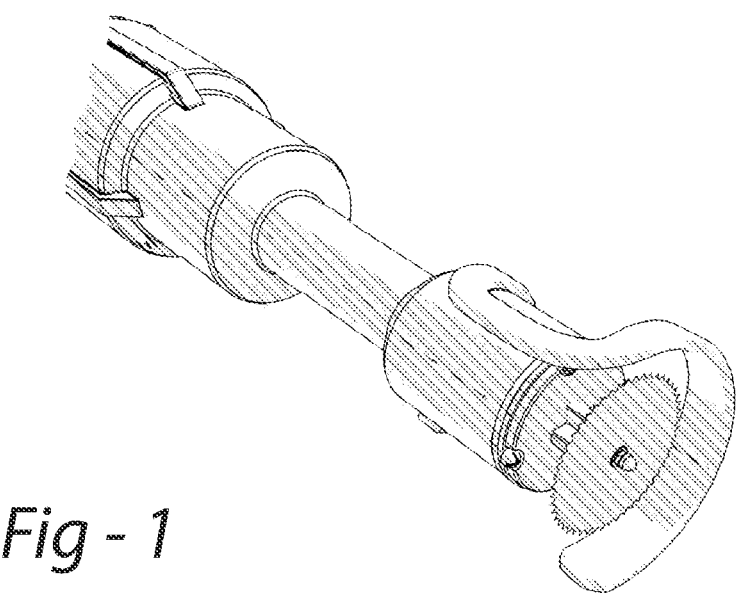
FIG. 1 is a partial environmental perspective view of the removable rubber bracelet for cast cutting, shown attached to a cast cutting saw.
Figure 2:
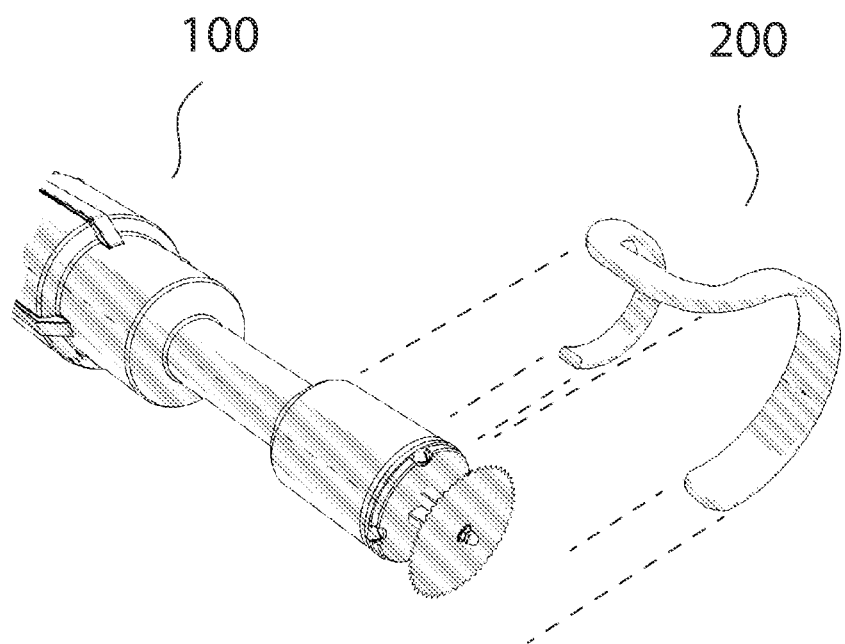
FIG. 2 is an exploded environmental perspective view of the removable rubber bracelet of Fig., shown detached from the cast cutting saw.

As shown in FIGS. 1-2, the RRB 200 is a single piece and doesn't need any additional components or steps for attaching and removing the RRB 200 from the cast cutting saw 100, and due to its flexible hard rubber material, provides safety, cost effectiveness, flexibility in size, and hygiene. The shape of the RRB 200 is designed to allow the blade of the cast cutting saw to start from anywhere and at any angle of the cast, overcoming the challenges that might occur with the various shapes of casts on different parts of the body. The RRB 200 provides a confined space to execute the cast removal process cutting step. With the RRB 200 being attached to the cast cutting saw 100, the cast removal process is safer, easier, faster, and more comfortable to the patient.

Figure 3:
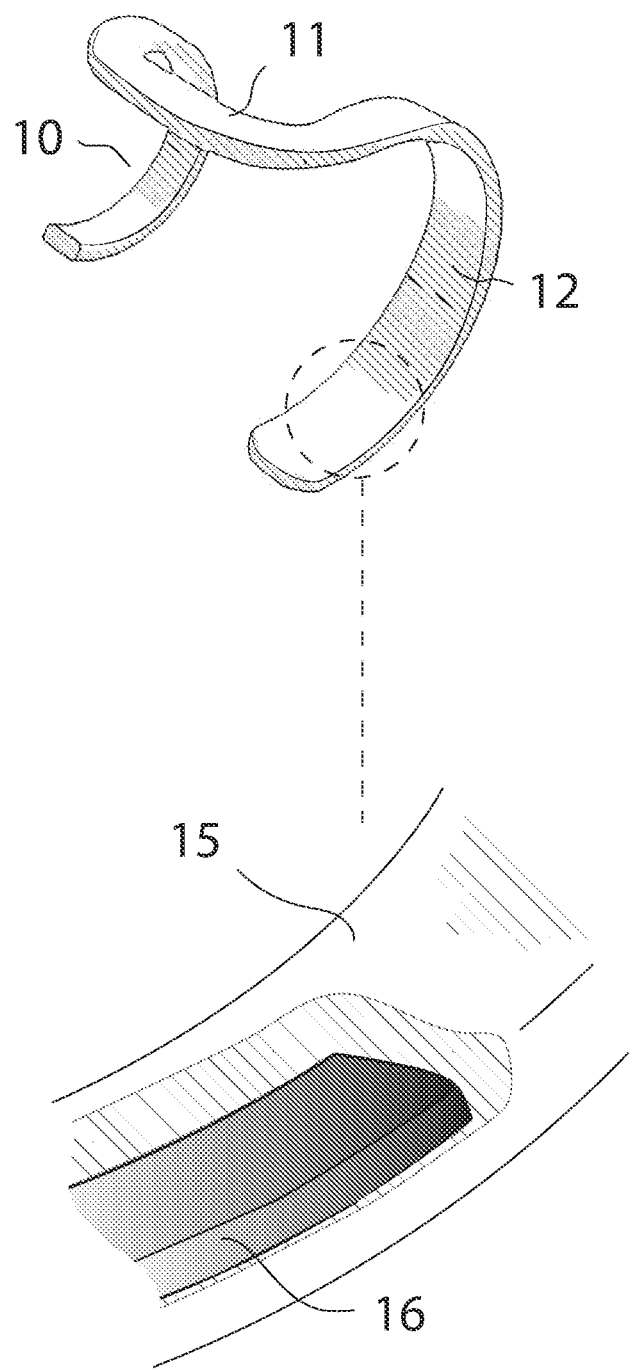
FIG. 3 is a perspective view of the removable rubber bracelet of FIG. 1, the inset showing a detail view partially broken away to show the inner core.

As shown in FIG. 3, the RRB 200 is a molded, hard, one-size fits all rubber piece that can snuggly attach to the cast cutting saw body using a smaller curved arm 10. The smaller curved arm 10 is connected to a larger curved arm 12 by a slightly arcing or outward tapering crossbar 11, the arms 10, 12 extending from opposite ends of the crossbar 11 parallel to each other. The larger curved arm 12 is a half-circle that sits around the cast cutting blade with enough space for the cast to be in the middle so that the saw blade spins freely while providing maximum protection for the skin. The RRB 200 is comprised of two layers, as shown in FIG. 3, an outer thick rubber layer 15 and an inner core of flexible or malleable material 16, where the inner flexible material 16 is a metal (i.e. copper or spring steel).

Figure 4:
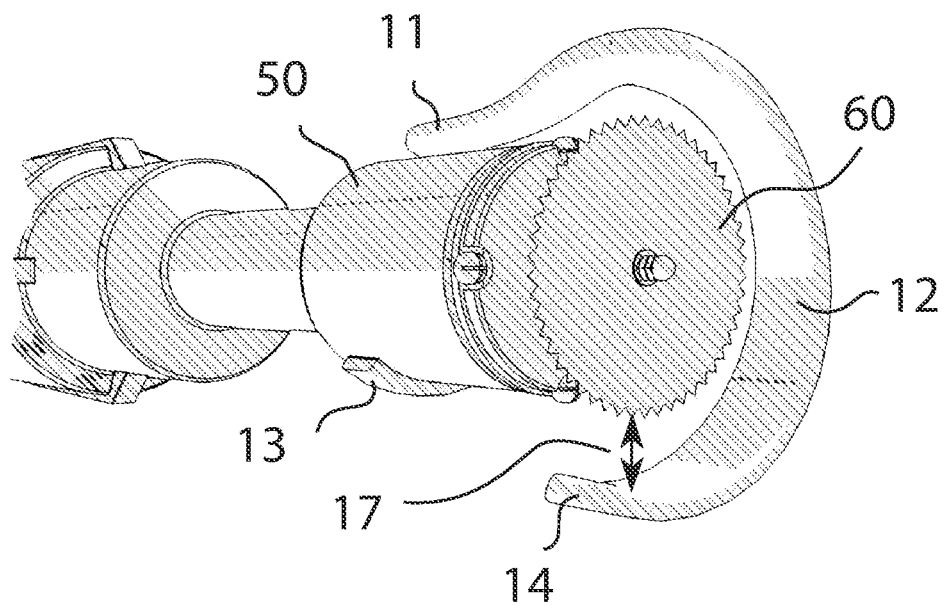
FIG. 4 is a partial environmental perspective view of the removable rubber bracelet f FIG. 1, as seen from below the blade.
Figure 5:
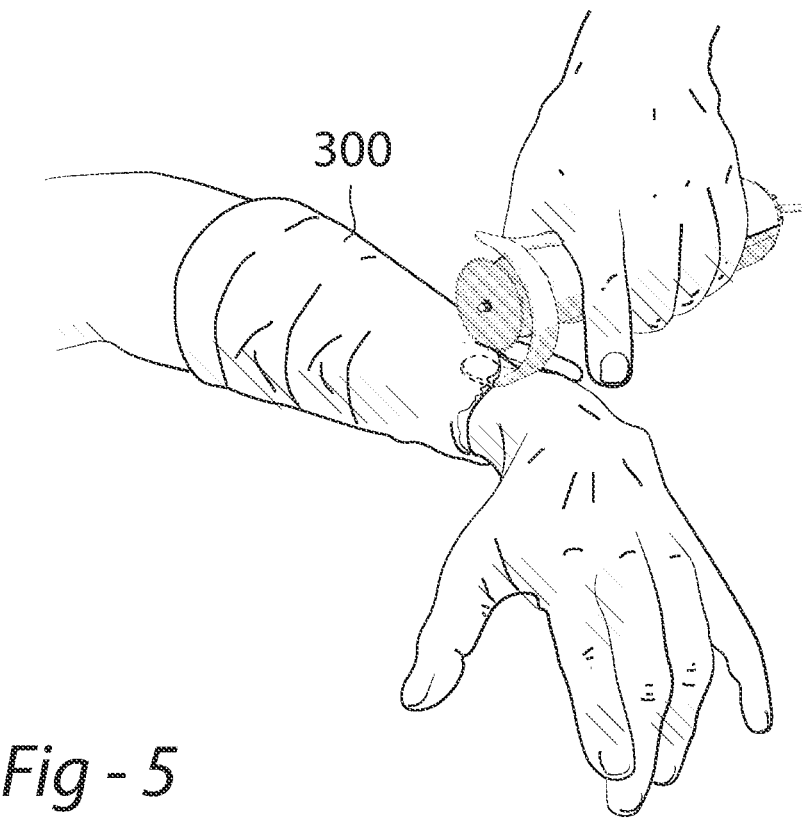
FIG. 5 is an environmental perspective view of the removable rubber bracelet of FIG. 1, shown during a cast cutting process.

As shown in FIGS. 3-5, the RRB 200 is attachable to the barrel 50 of the cast cutting saw 100. The RRB 200 attaches with a terminal end 13 of the smaller curved arm 10 gripping the barrel 50 and the slightly arcing crossbar 11 extending forward towards the blade. The inner surface of the larger curved arm 12 faces the blade of the cast cutting saw and terminates in a tip 14. Also shown is a clearing distance 17 between the rear and bottom circumference of the circular toothed blade 60 of the cast cutting saw 100 and the inner surface of the larger curved arm 12, which is supported in cantilever fashion by the crossbar 11. In FIG. 5, the process of using the RRB 200 where the cast on a body part of the patient, in this instance, a casted forearm and hand 300, is shown. The larger curved arm 12 is inserted between the cast and the patient's skin by means of the tip 14. The clearing distance 17 between the rear and bottom circumference of the circular toothed blade 60 of the cast cutting saw 100 and the inner surface of the larger curved arm 12 provides a safe confined area within which the circular toothed blade 60 can cut into the cast material without cutting into the skin below because of the shielding provided by the inner surface of the larger curved arm 12.

In addition to preventing both abrasive and thermal injuries, the RRB 200 is easy to implement, and as a result, improves hygiene. The RRB 200 can be a single use disposable device, and further, is usable with cast cutting saws of varying housing dimensions. The RRB 200 is also easy to clean and sterilize, and as a result, can also be a multiple use device. Additionally, it can be provided in various colors for improved aesthetics and can even be provided with a logo or personalization. For instance, the RRB 200 can be provided as a memento to the patient as commemoration of the patient's successful orthopedic treatment symbolized by the cast removal process.

It is to be understood that the removable rubber bracelet for cast cutting is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A removable rubber bracelet for cast cutting, comprising:
   a slightly tapering crossbar having opposite first and second ends;
   a smaller curved saw attachment arm extending from the first end of the crossbar, the smaller curved saw attachment arm being adapted for attachment to a cast cutting saw;
   a larger curved shielding arm extending from the second end of the crossbar parallel to the smaller curved saw attachment arm, the larger curved shielding arm being supported cantilever by the tapering crossbar and dimensioned and configured for extending at least partially around a blade of the cast cutting saw under and in rear of the blade and separated therefrom by a small gap, the bracelet being covered by an outer layer of rubber;
   whereby a patient is shielded from accidental cuts and thermal burns while a cast is removed by cutting the cast with the cast cutting saw.

2. The removable rubber bracelet as recited in claim 1, wherein the smaller curved saw attachment arm of the removable rubber bracelet is adapted for snapping onto a barrel of the cast cutting saw.

3. The removable rubber bracelet as recited in claim 1, wherein the removable rubber bracelet has an inner core made of a flexible, malleable metal material.

4. The removable rubber bracelet as recited in claim 3, wherein said inner core comprises copper.

5. The removable rubber bracelet as recited in claim 3, wherein said inner core comprises spring steel.

6. The removable rubber bracelet as recited in claim 1, wherein said larger curved shielding arm has a tip end usable as a safely guide when using the cast cutting saw across a top surface of the cast.

7. The removable rubber bracelet as recited in claim 1, wherein the removable rubber bracelet is a single-use disposable device.

8. The removable rubber bracelet as recited in claim 1, wherein said removable rubber bracelet is a multiple use device capable of being sterilized and cleaned for multiple uses.

9. The removable rubber bracelet as recited in claim 1, wherein the removable rubber bracelet can be provided in multiple colors.

\* \* \* \* \*